United States Patent
Sekoguchi

(10) Patent No.: US 8,624,476 B2
(45) Date of Patent: Jan. 7, 2014

(54) ION-GENERATING DEVICE AND ELECTRICAL APPARATUS

(75) Inventor: Yoshinori Sekoguchi, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 258 days.

(21) Appl. No.: 13/002,752

(22) PCT Filed: Jun. 30, 2009

(86) PCT No.: PCT/JP2009/061909
§ 371 (c)(1),
(2), (4) Date: Jan. 5, 2011

(87) PCT Pub. No.: WO2010/013570
PCT Pub. Date: Feb. 4, 2010

(65) Prior Publication Data
US 2011/0115362 A1 May 19, 2011

(30) Foreign Application Priority Data
Jul. 31, 2008 (JP) .................. 2008-197864

(51) Int. Cl.
*H01J 27/00* (2006.01)

(52) U.S. Cl.
USPC .......................................... 313/230

(58) Field of Classification Search
USPC ................... 313/230, 362.1, 359.1
See application file for complete search history.

(56) References Cited

U.S. PATENT DOCUMENTS

2010/0001205 A1   1/2010  Sekoguchi et al.

FOREIGN PATENT DOCUMENTS

| EP | 1 625 890 A2 | 2/2006 |
| JP | 7-42096 U | 7/1995 |
| JP | 10-199653 A | 7/1998 |
| JP | 2001-189199 A | 7/2001 |
| JP | 2003-163067 A | 6/2003 |
| JP | 2003-308947 A | 10/2003 |
| JP | 2007-236470 A | 9/2007 |
| JP | 2008-53000 A | 3/2008 |
| JP | 2008-123917 A | 5/2008 |
| KR | 2001-0051161 A | 6/2001 |
| KR | 20010051161 A * | 6/2001 |
| RU | 2021822 C1 | 10/1994 |

* cited by examiner

*Primary Examiner* — Anh Mai
*Assistant Examiner* — Brenitra M Lee
(74) *Attorney, Agent, or Firm* — Birch, Stewart, Kolasch & Birch, LLP

(57) ABSTRACT

An ion-generating device includes a discharge electrode and an induction electrode. The discharge electrode has a needle-like tip. The induction electrode has a circular through hole. The tip of the discharge electrode penetrates the through hole of the induction electrode, and protrudes upward with respect to an upper surface of the induction electrode. It is thereby possible to obtain an ion-generating device capable of improving ion emission efficiency, and an electrical apparatus provided with the ion-generating device.

9 Claims, 7 Drawing Sheets

IN THE CASE WHERE e = 0

ION-GENERATING DEVICE AND ELECTRICAL APPARATUS

TECHNICAL FIELD

The present invention relates to an ion-generating device and an electrical apparatus, and particularly relates to an ion-generating device including an induction electrode and a discharge electrode having a needle-like tip, for generating ions by discharge, and an electrical apparatus provided with the ion-generating device.

BACKGROUND ART

Many ion-generating devices that utilize a discharge phenomenon have been commercialized. These ion-generating devices are generally configured with an ion-generating element for generating ions, a high-voltage transformer for supplying a high voltage to the ion-generating element, a high voltage-generating circuit for driving the high-voltage transformer, and a power supply input unit such as a connector.

An example of the commercialized ion-generating elements includes the one that uses a metal wire, a metal plate having an acute-angled portion, a needle-like metal, or the like as a discharge electrode, and uses a metal plate, a grid, or the like at a ground potential as an induction electrode (counter electrode), or the one that uses the ground as an induction electrode and does not particularly dispose an induction electrode. In the ion-generating element of this type, the air serves as an insulator. This ion-generating element utilizes a scheme to produce a discharge phenomenon by causing electric field concentration at a tip of an electrode, which has an acute-angled portion such as a needle-like portion to serve as a discharge electrode, when applying a high voltage to the electrode, and causing an electrical breakdown of the air in close vicinity of the tip.

An example of the ion-generating elements that utilize this scheme is a device disclosed in, for example, Japanese Patent Laying-Open No. 10-199653. This publication discloses a device which includes a discharge electrode provided with a needle-like metal, and a cylindrical electrode provided to face the discharge electrode, and serves for extracting negative ions generated as corona discharge occurs, to an outside of the device.

For another example, there is a device disclosed in Japanese Patent Laying-Open No. 2003-308947. The publication describes a configuration in which an induction electrode is disposed rearward (in a lateral surface position) with respect to a tip portion of a discharge electrode needle. The above publication discloses that the shape of the induction electrode may also be of a stick type, a plate type, a mesh type, or the like, and that the key point is not the shape of the induction electrode but the disposition thereof.

DOCUMENT LIST

Patent Document

Patent Document 1: Japanese Patent Laying-Open No. 10-199653
Patent Document 2: Japanese Patent Laying-Open No. 2003-308947

SUMMARY OF THE INVENTION

Problems to be Solved by the Invention

Positive ions and negative ions generated by discharge disappear by being recombined at a moment of production, by being neutralized when a positively-applied or negatively-applied electrode attracts the ions having a reverse polarity, or by being neutralized by collision between positive ions and negative ions in a space, and the like.

The ion-generating device aims to generate more ions and emit them to a space. A challenge to be tackled is to how to reduce the recombination and neutralization between positive ions and negative ions, as described above.

Here, in the device disclosed in Japanese Patent Laying-Open No. 10-199653, the negative ions generated by corona discharge are trapped at a wall surface in the cylindrical electrode, so that ion emission efficiency is decreased.

In the configuration disclosed in Japanese Patent Laying-Open No. 2003-308947, directivity of a distribution of an electric field, which is directed from the tip portion of the discharge electrode needle toward the induction electrode disposed rearward (in the lateral surface position) with respect to the discharge electrode needle, becomes nonuniform. Because of the nonuniformity of the electric field distribution, moving directions of ions also become nonuniform, so that ion emission efficiency is decreased. In addition, discharge at the discharge electrode tip becomes unstable, so that ion generation efficiency is decreased.

As to the size of the ion-generating device itself; if the ion-generating device occupies a smaller area, it achieves a wider range of uses, and when it is assumed to be mounted on an electrical apparatus, restrictions to be imposed when it is disposed in the apparatus become fewer. Further, in addition to the area to be occupied as described above, the thickness of the ion-generating device is preferably decreased as well, because not a few apparatuses have a narrow air blow passage.

In brief, a challenge is to, based on the premise that positive and negative ions are delivered by the blown air, cause stable discharge at the discharge electrode tip and improve ion generation efficiency, by decreasing the rate at which ions generated by discharge at the discharge electrode tip are trapped by the induction electrode and neutralized and by generating a uniform electric field, so as to eventually achieve significant increase in number of ions to be emitted.

Furthermore, from a viewpoint of shape and structure, a challenge is to implement an ion-generating device which has a minimum thickness and has an ion-generating element and a drive circuit integrated therein in a compact shape, in consideration of fixed positions of the discharge electrode and the induction electrode, prevention of creeping discharge of the induction electrode and the discharge electrode, protection of the discharge electrode tip, degree of freedom in mounting on an apparatus, and others.

The present invention has been made in view of the above-described challenges, and an object of the present invention is to provide an ion-generating device capable of improving ion emission efficiency, and an electrical apparatus provided with the ion-generating device.

Another object of the present invention is to provide an ion-generating device capable of improving ion emission efficiency and suitable for compactness and reduction in thickness, and an electrical apparatus provided with the ion-generating device.

Means for Solving the Problems

One ion-generating device in the present invention is an ion-generating device for generating ions by discharge, including: a discharge electrode; and an induction electrode. The discharge electrode has a needle-like tip. The induction electrode has a flat plate portion at which a circular through hole is made. The tip of the discharge electrode penetrates the through hole of the induction electrode, and protrudes upward with respect to an upper surface of the flat plate portion of the induction electrode.

According to the one ion-generating device in the present invention, the tip of the discharge electrode penetrates the circular through hole of the induction electrode, and an outer portion of the discharge electrode is surrounded by the induction electrode. Therefore, it becomes possible to generate an electric field from the needle-like tip of the discharge electrode, which serves as the center, toward the induction electrode along the entire circumference, namely, over 360° in plan view, and suppress nonuniformity of the directivity of an electric field distribution. Accordingly, it is possible to suppress nonuniformity of the ion moving directions, which is caused by the nonuniformity of the electric field distribution, and hence it is possible to improve ion emission efficiency and cause stable discharge at the discharge electrode tip, resulting in improvement in ion generation efficiency.

Furthermore, the tip of the discharge electrode penetrates the through hole of the induction electrode, and protrudes upward with respect to the upper surface of the flat plate portion of the induction electrode. Therefore, it is possible to decrease the rate at which ions generated by discharge at the discharge electrode tip are trapped by the induction electrode and neutralized, and increase an amount of emitted ions.

Another ion-generating device in the present invention is an ion-generating device for generating ions by discharge, including: an ion-generating element; a high-voltage transformer; a high voltage-generating circuit; a power supply input connector; and a casing. The ion-generating element includes a discharge electrode having a needle-like tip, and an induction electrode having a flat plate portion at which a circular through hole is made. The high-voltage transformer is for supplying a high voltage to the ion-generating element. The high voltage-generating circuit is for driving the high-voltage transformer. The power supply input connector is electrically connected to the high voltage-generating circuit. The ion-generating element, the high-voltage transformer, the high voltage-generating circuit, and the power supply input connector are disposed in the casing. The tip of the discharge electrode penetrates the through hole of the induction electrode, and protrudes upward with respect to an upper surface of the flat plate portion of the induction electrode. The ion-generating element, the high-voltage transformer, the high voltage-generating circuit, and the power supply input connector are disposed in a planar manner with respect to one another, and disposed in the casing in an integrated manner.

According to the other ion-generating device in the present invention, the tip of the discharge electrode penetrates the circular through hole of the induction electrode, and the outer portion of the discharge electrode is surrounded by the induction electrode. Therefore, it becomes possible to generate an electric field from the needle-like tip of the discharge electrode, which serves as the center, toward the induction electrode along the entire circumference, namely, over 360° in plan view, and suppress nonuniformity of the directivity of an electric field distribution. Therefore, it is possible to suppress nonuniformity of ion moving directions caused by the nonuniformity of an electric field distribution, and hence it is possible to improve ion emission efficiency and cause stable discharge at the tip of the discharge electrode, resulting in improvement in ion generation efficiency.

The tip of the discharge electrode penetrates the through hole of the induction electrode and protrudes upward with respect to the upper surface of the flat plate portion of the induction electrode. Therefore, it is possible to decrease the rate at which ions generated by discharge at the tip of the discharge electrode are trapped by the induction electrode and neutralized, and increase an amount of emitted ions.

Furthermore, the ion-generating element, the high-voltage transformer, the high voltage-generating circuit, and the power supply input connector are disposed in a planar manner with respect to one another, and disposed in the casing in an integrated manner, so that it is possible to make the ion-generating device thin and compact.

Preferably, the one and the other ion-generating devices further include a casing in which the discharge electrode and the induction electrode are disposed. The casing has a top plate at which an ion-emitting hole in communication with the through hole of the induction electrode is formed. The tip of the discharge electrode is disposed such that the tip does not protrude upward with respect to a top surface of the top plate.

It is thereby possible to suppress deterioration in ion generation performance of the discharge electrode due to mechanical impact. Furthermore, it is possible to prevent direct hand contact with the discharge electrode serving as a high-voltage unit, and prevent electric shock.

Preferably, in the one and the other ion-generating devices described above, a length by which the tip of the discharge electrode protrudes upward with respect to the upper surface of the flat plate portion of the induction electrode is shorter than a radius of the through hole.

It is thereby possible to prevent discharge that occurs not at the tip of the discharge electrode, but at a trunk portion of the discharge electrode, at which a distance from the induction electrode is the shortest, and it is possible to suppress decrease in ion emission efficiency.

Preferably, the one and the other ion-generating devices further include a supporting substrate supporting the induction electrode. The induction electrode has a bent portion made by bending the flat plate portion and supported by the supporting substrate. The induction electrode is supported by the supporting substrate such that a gap is made between the flat plate portion of the induction electrode and the supporting substrate.

It is thereby possible to suppress creeping discharge caused along a surface of the supporting substrate between the induction electrode and the discharge electrode.

An electrical apparatus in the present invention includes: any of the ion-generating devices described above; and an air blow unit for delivering at least any of positive ions and negative ions generated at the ion-generating device on a blown air stream to an outside of the electrical apparatus.

According to the electrical apparatus in the present invention, it is possible to deliver ions generated at the ion-generating device on an air stream by the air blow unit. Therefore, it is possible, for example, to emit ions to an outside of an air-conditioning apparatus, and emit ions to an inside or an outside of a cooling apparatus.

Effects of the Invention

As described above, according to the present invention, the tip of the discharge electrode penetrates the through hole of the induction electrode and protrudes upward with respect to the upper surface of the induction electrode, so that ion emission efficiency can be improved.

BRIEF DESCRIPTION OF THE DRAWINGS

FIG. 13 (B) is a drawing that shows the state where the protruding length of the discharge electrode from the induction electrode is longer than a radius of the through hole. FIG. 13 (C) is a drawing that shows the state where the protruding length of the discharge electrode from the induction electrode is shorter than a radius of the through hole.

MODES FOR CARRYING OUT THE INVENTION

An embodiment of the present invention will hereinafter be described based on the drawings.

Figure 1:
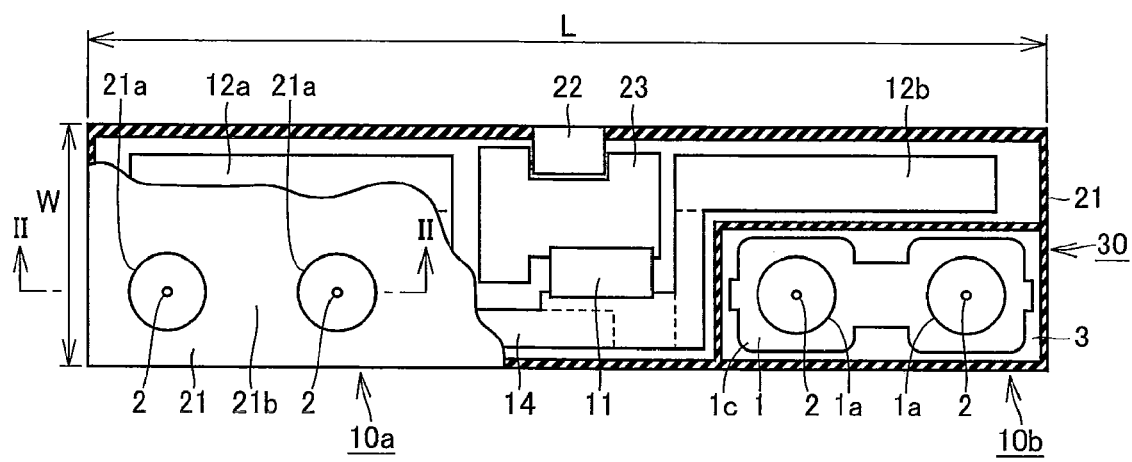
FIG. 1 is a schematic plan view that schematically shows a configuration of an ion-generating device in an embodiment of the present invention, and a partially cut-away plan view that shows a part of a top plate of a casing in a cut-away manner, and a molding resin in perspective.
Figure 2:
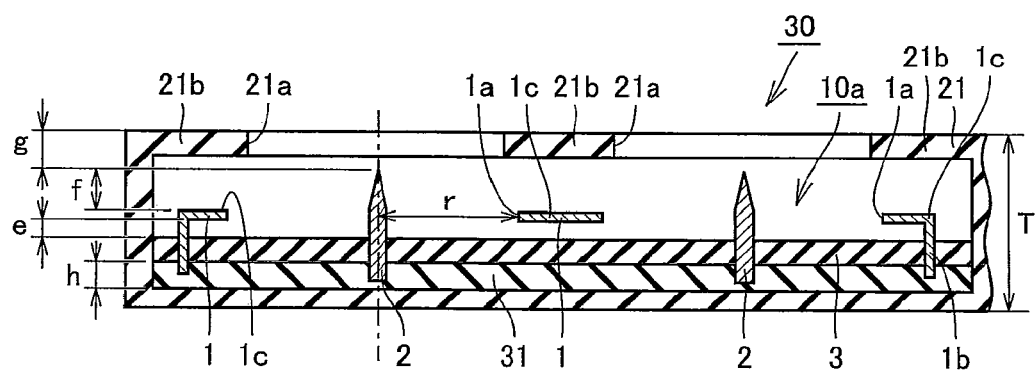
FIG. 2 is a schematic cross-sectional view taken along a line II-II in FIG. 1.
Figure 3:
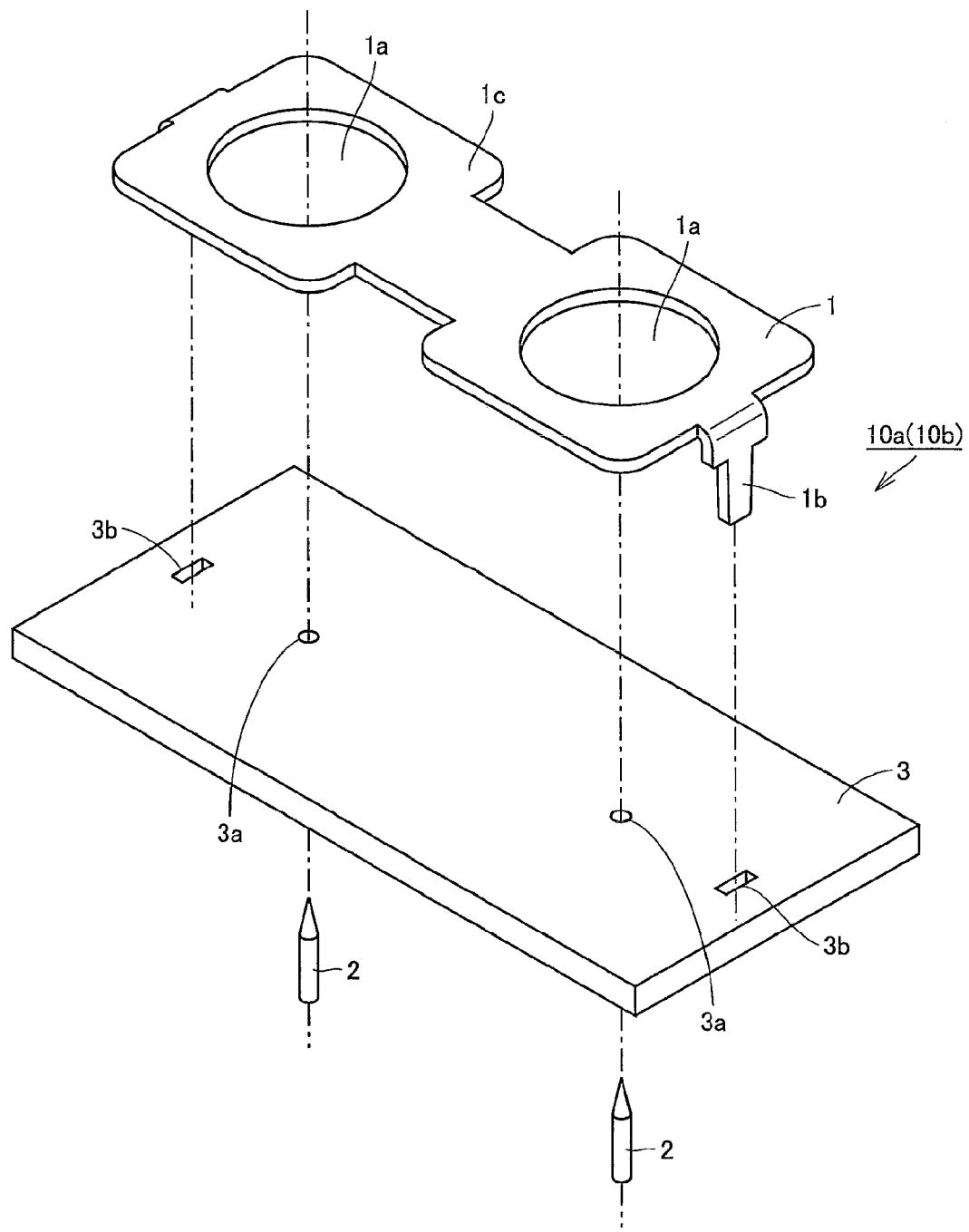
FIG. 3 is an exploded perspective view that shows a configuration of an ion-generating element shown in FIGS. 1 and 2.
Figure 4:
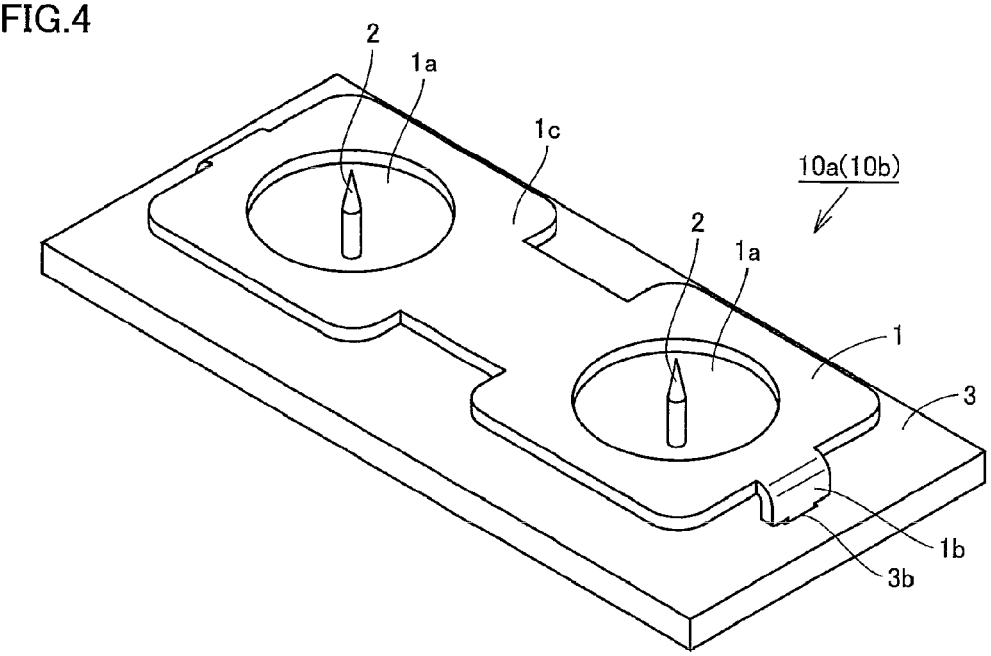
FIG. 4 is a perspective assembly view that shows the configuration of the ion-generating element shown in FIGS. 1 and 2.

FIG. 1 is a schematic plan view that schematically shows a configuration of an ion-generating device in an embodiment of the present invention, and a partially cut-away plan view that shows a part of a top plate of a casing in a cut-away manner, and a molding resin in perspective. FIG. 2 is a schematic cross-sectional view taken along a line II-II in FIG. 1. FIGS. 3 and 4 are an exploded perspective view and a perspective assembly view, respectively, that show a configuration of an ion-generating element used in the ion-generating device shown in FIGS. 1 and 2.

With reference to FIG. 1, an ion-generating device 30 in the present embodiment mainly has an outer casing 21, an ion-generating element 10a for generating positive ions, an ion-generating element 10b for generating negative ions, a high-voltage transformer 11, high-voltage circuits 12a, 12b, a power supply circuit (high voltage-generating circuit) 23, and a power supply input connector 22.

Ion-generating element 10a is disposed on one end side (on the left in FIG. 1) in outer casing 21, and ion-generating element 10b is disposed on the other end side (on the right in FIG. 1) in outer casing 21. By integrally disposing ion-generating elements 10a, 10b, high-voltage transformer 11, high-voltage circuits 12a, 12b, power supply circuit 23, and power supply input connector 22 in outer casing 21, and by disposing high-voltage transformer 11, high-voltage circuits 12a, 12b, power supply circuit 23, and power supply input connector 22 in a space between ion-generating elements 10a and 10b, it is possible to achieve high disposition efficiency and make ion-generating device 30 compact. Further, by disposing ion-generating elements 10a, 10b, high-voltage transformer 11, high-voltage circuits 12a, 12b, power supply circuit 23, and power supply input connector 22 in outer casing 21 in a planar manner, it is possible to make ion-generating device 30 thin.

Both of positive high-voltage circuit 12a and negative high-voltage circuit 12b are supported on the same substrate 14. Positive high-voltage circuit 12a is disposed on one end side (on the left in FIG. 1) in casing 21 such that it is adjacent to ion-generating element 10a for generating positive ions. Negative high-voltage circuit 12b is disposed on the other end side (on the right in FIG. 1) in casing 21 such that it is adjacent to ion-generating element 10b for generating negative ions. A part of substrate 14, which supports high-voltage circuits 12a, 12b, is located between ion-generating elements 10a, 10b. It is noted that a substrate supporting positive high-voltage circuit 12a and a substrate supporting negative high-voltage circuit 12b may be separated from each other.

With reference to FIGS. 3 and 4, ion-generating elements 10a, 10b are for generating positive ions and negative ions, respectively, by corona discharge, for example, and have an induction electrode 1, a discharge electrode 2, and a supporting substrate 3.

Induction electrode 1 is made of a one-piece metal plate, and has a plurality of (e.g. two) through holes 1a each having a shape of approximately a perfect circle provided at a flat plate portion to correspond to the number of discharge electrodes 2. With each of through holes 1a, it is possible to generate an electric field uniform over 360° at the tip of discharge electrode 2 and cause stable corona discharge. The flat plate portion of induction electrode 1 is made of a sheet metal with a hole, and a portion of the flat plate portion other than through hole 1a has a uniform thickness.

Induction electrode 1 has a bent portion 1b at each of opposite end portions, for example, bent portion 1b being made by bending a part of the metal plate at approximately a right angle with respect to the flat plate portion. Bent portion 1b has a large-width supporting portion and a small-width inserted portion. The above-described supporting portion has one end linked to the flat plate portion, and the other end linked to the above-described inserted portion.

Discharge electrode 2 has a needle-like tip. Supporting substrate 3 has a through hole 3a for allowing discharge electrode 2 to be inserted therethrough, and a through hole 3b for allowing the inserted portion of bent portion 1b to be inserted therethrough.

Needle-like discharge electrode 2 is supported by supporting substrate 3 while being inserted or press-fitted into through hole 3a and penetrating supporting substrate 3. Consequently, one end of discharge electrode 2, which is a needle-like end, protrudes on a front surface side (an ion-generating unit side) of supporting substrate 3. To the other end of discharge electrode 2, which protrudes on a back surface side (a soldering surface side) of supporting substrate 3, it is possible to electrically connect a lead wire or a wiring pattern with use of solder (not shown).

The inserted portion of induction electrode 1 is supported by supporting substrate 3 while being inserted into through hole 3b and penetrating supporting substrate 3. To a tip of the inserted portion, which protrudes on the back surface side of supporting substrate 3, it is possible to electrically connect a lead wire or a wiring pattern with use of solder (not shown). Further, in the state where induction electrode 1 is supported by supporting substrate 3, discharge electrode 2 is disposed such that its needle-like tip is located approximately at the center of through hole 1a having a shape of approximately a perfect circle in plan view as shown in FIG. 1. Thereby, the distance between the needle-like tip of discharge electrode 2 and an outer peripheral portion of circular through hole 1a is kept constant along the entire circumference of through hole 1a.

Discharge electrode 2 in ion-generating element 10a for generating positive ions serves as a positive discharge electrode, and cooperates with induction electrode 1 in ion-generating element 10a to configure a positive ion-generating unit (positive electrode pair). Discharge electrode 2 in ion-generating element 10b for generating negative ions serves as a negative discharge electrode, and cooperates with induction electrode 1 in ion-generating element 10b to configure a negative ion-generating unit (negative electrode pair).

Furthermore, in each of ion-generating elements 10a, 10b, there is provided induction electrode 1 common to the plurality of discharge electrodes 2 for generating ions of the same polarity, namely, any of a positive polarity and a negative polarity. Specifically, ion-generating element 10a for generating positive ions is provided with induction electrode 1 common to two positive discharge electrodes 2, for example, and induction electrode 1 is provided with two through holes 1a to correspond to the number of positive discharge electrodes 2. As such, ion-generating element 10a for generating positive ions is configured such that it is capable of generating positive ions at a plurality of (e.g. two) positive ion-generating units.

In ion-generating element 10b for generating negative ions, there is provided induction electrode 1 common to two negative discharge electrodes 2, for example, and induction electrode 1 is provided with two through holes 1a to correspond to the number of negative discharge electrodes 2. As such, ion-generating element 10b for generating negative ions is configured such that it is capable of generating negative ions at a plurality of (e.g. two) negative ion-generating units. It is noted that one ion-generating element may have one discharge electrode 2, and may also have three or more discharge electrodes 2.

With reference to FIG. 2, the needle-like tip of discharge electrode 2 penetrates through hole 1a of induction electrode 1, and protrudes upward with respect to an upper surface 1c of the flat plate portion of induction electrode 1. A length f by which the needle-like tip of discharge electrode 2 protrudes upward with respect to upper surface 1c of the flat plate portion of induction electrode 1 is shorter than a radius r of through hole 1a.

The needle-like tip of discharge electrode 2 is disposed such that it does not protrude upward with respect to a top surface of a top plate 21b of outer casing 21, and the needle-like tip of discharge electrode 2 is located at a site retracted from the top surface of top plate 21b by, for example, a distance g. It is thereby possible to suppress deterioration of ion generation performance of discharge electrode 2 due to mechanical impact, and prevent direct hand contact with discharge electrode 2, which serves as a high-voltage unit, to prevent electric shock.

Furthermore, induction electrode 1 is supported by supporting substrate 3 such that a gap having a dimension e is formed between the flat plate portion of induction electrode 1 and supporting substrate 3. It is thereby possible to prevent creeping discharge caused along a surface of supporting substrate 3 between induction electrode 1 and discharge electrode 2. Furthermore, on the soldering surface side of supporting substrate 3, there is also provided a space having a dimension h that is sufficient enough for preventing a soldered portion or the like of the parts from being in contact with outer casing 21.

The soldering surface side of supporting substrate 3 (i.e. the space having dimension h in FIG. 2) is molded with a molding resin (e.g. an epoxy resin) 31. Although not shown, it is preferable that the high-voltage transformer, the high-voltage circuit, and the power supply circuit are also molded with a molding resin.

An ion-emitting hole 21a is provided at top plate 21b of outer casing 21 above discharge electrode 2. By power distribution, there is generated an electric field directed from the needle-like tip of discharge electrode 2 to induction electrode 1, and the electric field also expands to an outside of ion-emitting hole 21a. By delivering a blown air thereto, it is possible to emit positive and negative ions on the blown air to an outer space of ion-generating device 30.

It is advantageous to set the size of the entire ion-generating device 30 to be as small and thin as possible, so as to be mounted on wide variety of electrical apparatuses. Therefore, ion-generating device 30 preferably has a thickness T (FIG. 2) of 10 mm or less, and an area L×W (FIG. 1) of approximately 100 mm×20 mm-150 mm×40 mm.

Next, description will be made on how respective functional elements are electrically connected.

Figure 5:
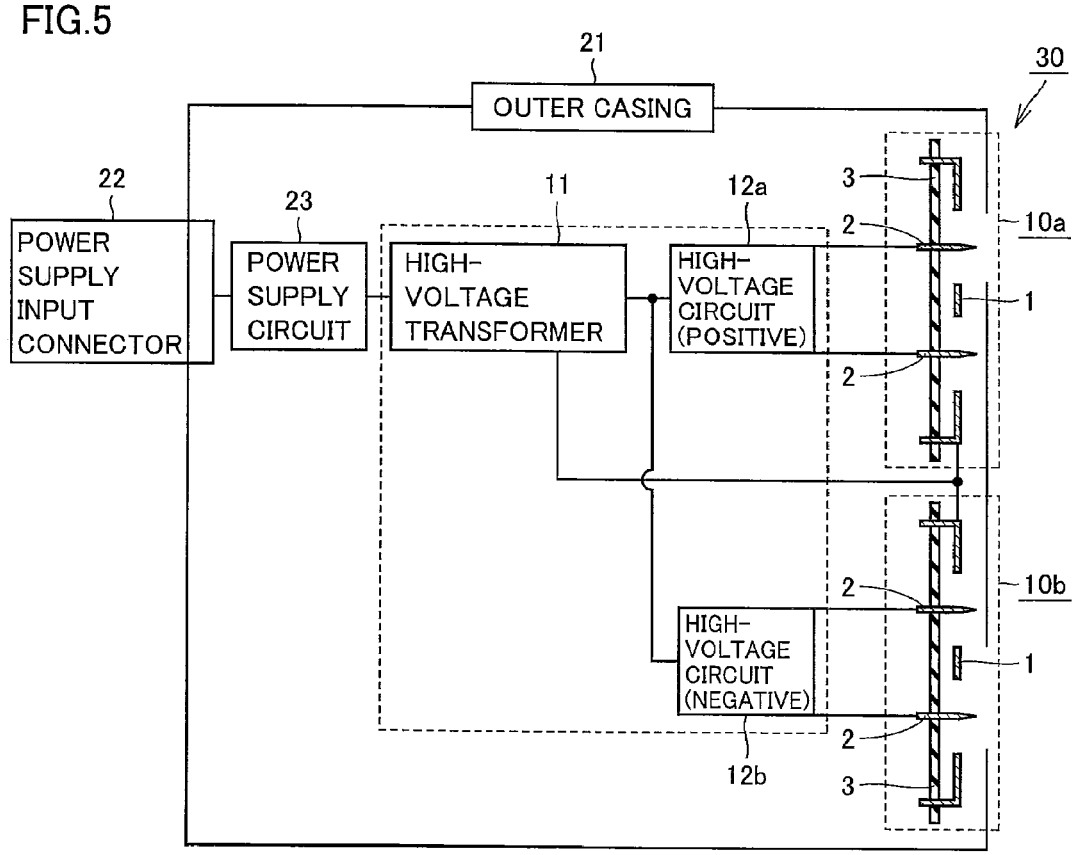
FIG. 5 is a functional block diagram of the ion-generating device in the embodiment of the present invention, and shows how functional elements are electrically connected.

FIG. 5 is a functional block diagram of the ion-generating device in the embodiment of the present invention, and shows how the functional elements are electrically connected. With reference to FIG. 5, ion-generating device 30 includes outer casing 21, ion-generating elements 10a, 10b, high-voltage transformer 11, high-voltage circuits 12a, 12b, power supply input connector 22, and power supply circuit 23, as described above. It is noted that power supply input connector 22 is structured such that a part thereof is disposed in outer casing 21, and another part thereof is exposed to an outside of outer casing 21, to thereby allow a power supply to be connected thereto via a connector from an outside.

Power supply input connector 22 is a portion for receiving a direct-current power supply or a commercial alternating-current power supply, which serves as an input power supply. Power supply input connector 22 is electrically connected to power supply circuit 23. Power supply circuit 23 is electrically connected to a primary side of high-voltage transformer 11. High-voltage transformer 11 is for stepping up a voltage inputted to the primary side, and outputting the stepped-up voltage to the secondary side. One end of the secondary side of high-voltage transformer 11 is electrically connected to induction electrode 1 of each of ion-generating elements 10a, 10b. The other end of the secondary side of high-voltage transformer 11 is electrically connected via positive high-voltage circuit 12a to positive discharge electrodes 2 of ion-generating element 10a for generating positive ions, and electrically connected via negative high-voltage circuit 12b to negative discharge electrodes 2 of ion-generating element 10b for generating negative ions. It is noted that induction electrodes 1 in ion-generating elements 10a, 10b are electrically connected to each other to have the same potential.

Positive high-voltage circuit 12a is configured to apply to positive discharge electrode 2 a high voltage having a positive polarity with respect to induction electrode 1, and negative high-voltage circuit 12b is configured to apply to negative discharge electrode 2 a high voltage having a negative polarity with respect to induction electrode 1. It is thereby possible to generate dual-polarity ions, namely, positive ions and negative ions.

A high voltage is applied between induction electrode 1 and discharge electrode 2. When the tip of discharge electrode 2 reaches a certain electric field intensity or above, discharge occurs.

Although ion-generating device 30 described above can emit single-polarity ions, the present embodiment is based on the premise that bipolar ions, namely, positive ions and negative ions are emitted. Positive ions are generated by causing positive corona discharge at the tip of positive discharge electrodes 2, and negative ions are generated by causing negative corona discharge at the tip of negative discharge electrodes 2. A waveform to be applied is not particularly limited herein, and a direct current, an alternating-current waveform biased positively or negatively, a pulse waveform biased positively or negatively, or the like, having a high voltage is used. A waveform having a high voltage may be of any form, such as an alternating-current waveform, a direct-current waveform, a pulse waveform, or a waveform of combination thereof, and means a voltage that causes an electric field intensity that enables the occurrence of a discharge phenomenon. A voltage value is selected to fall within a voltage range that sufficiently causes discharge and enables generation of prescribed ion species.

Here, positive ions intended by the inventor are cluster ions each of which is identified as a hydrogen ion (H$^+$) having a plurality of water molecules attached therearound, and are represented as H$^+$(H$_2$O)$_m$ (m is a natural number). Negative ions are cluster ions each of which is identified as an oxygen ion (O$_2^-$) having a plurality of water molecules attached therearound, and are represented as O$_2^-$(H$_2$O)$_n$ (n is a natural number). Further, by generating approximately the same amount of H$^+$(H$_2$O)$_m$ (m is a natural number), which are identified as positive ions in the air, and O$_2^-$(H$_2$O)$_n$ (n is a natural number), which are identified as negative ions in the air, both types of ions attach to and surround funguses and viruses floating in the air. With the action of hydroxyl radicals (.OH) generated at that time, which are identified as active species, the floating funguses and others can be eliminated.

Next, description will be made on a configuration of an air-cleaning unit, which is an example of the electrical apparatus that uses the above-described ion-generating device.

In an electrical apparatus such as the air-cleaning unit, a fan mounted on the electrical apparatus is used for air blowing. The air-cleaning unit is for allowing the air, which has been taken in through an air inlet, to pass through a filter for cleaning, and supplying the cleaned air from the outlet port to an outside through a fan casing.

Figure 6:
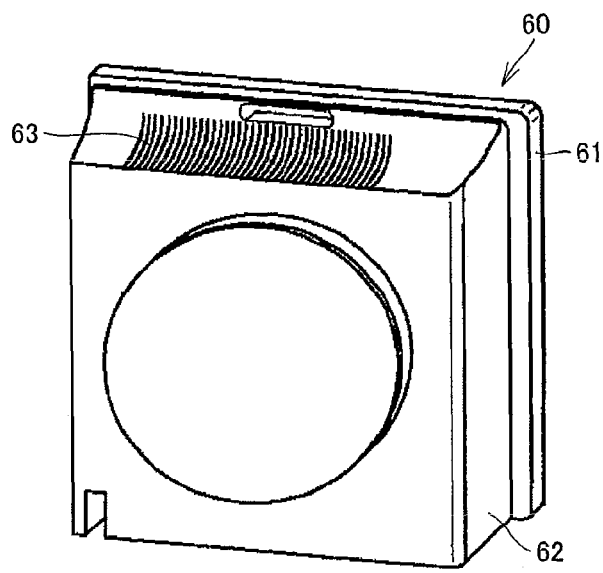
FIG. 6 is a perspective view that schematically shows a configuration of an air-cleaning unit that uses the ion-generating device shown in FIGS. 1 and 2.
Figure 7:
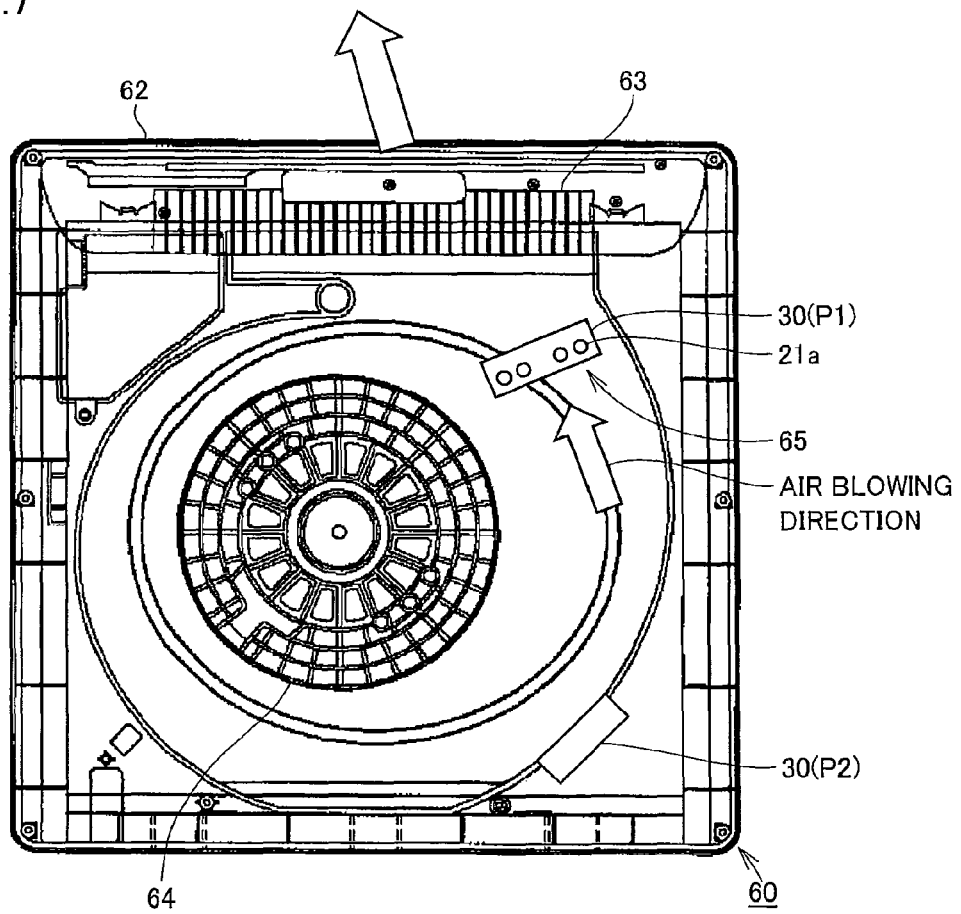
FIG. 7 is an exploded view of the air-cleaning unit shown in FIG. 6, showing how the ion-generating device is disposed therein.

FIG. 6 is a perspective view that schematically shows a configuration of the air-cleaning unit that uses the ion-generating device shown in FIGS. 1 and 2. FIG. 7 is an exploded view of the air-cleaning unit shown in FIG. 6, showing how the ion-generating device is disposed therein.

With reference to FIGS. 6 and 7, an air-cleaning unit 60 has a front panel 61 and a body 62. A rear top portion of body 62 is provided with an outlet port 63, through which clean air containing ions are supplied to the room. An air intake port 64 is formed at the center of body 62. The air taken in through air intake port 64 located at the front of air-cleaning unit 60 is cleaned by passing through a filter not shown. The cleaned air is supplied from outlet port 63 to the outside through a fan casing 65.

Ion-generating device 30 shown in FIGS. 1 and 2 is attached to a part of fan casing 65 that forms a passage of the cleaned air. Ion-generating device 30 is disposed to be able to emit ions through hole 21a, which serves as an ion-emitting unit, onto the flow of the above-described air. Exemplary dispositions of ion-generating device 30 may include a position P1 relatively close to outlet port 63, a position P2 relatively far from outlet port 63, and other positions, within the passage of the air. By allowing the blown air to pass through ion-emitting hole 21a in ion-generating device 30 as such, it becomes possible to supply ions, along with clean air, through outlet port 63 to the outside.

With air-cleaning unit 60 according to the present embodiment, ions generated at ion-generating device 30 can be delivered on the air stream by the air blow unit (air passage), so that it is possible to emit ions with cleaned air, to an outside of the unit. It is thereby possible to allow the air-cleaning unit to have an ion-generating function.

Further, ion-generating device 30 in the present embodiment is thin, so that even if it is mounted on the above-described electrical apparatus, it does not interfere with the blown air. Accordingly, it is possible to suppress noise generation and air volume decrease, and enable the ion-generating device to be mounted on and applied to multiple types of products.

In the present embodiment, an air-cleaning unit has been described as an example of the electrical apparatus. However, the present invention is not limited thereto. The electrical apparatus may also be, in addition to the air-cleaning unit, an air-conditioning unit (air-conditioner), a cooling apparatus, a vacuum cleaner, a humidifier, a dehumidifier, and the like, as long as it is an electrical apparatus that has an air blow unit for delivering ions on the air stream.

Next, description will be made on functional effects of the present embodiment.

Initially, according to the present embodiment, the tip of discharge electrode 2 penetrates circular through hole 1a of induction electrode 1, and an outer portion (the entire outer peripheral surface) of discharge electrode 2 is surrounded by induction electrode 1, so that it is possible to improve ion emission efficiency and ion generation efficiency. This feature will hereinafter be described.

Figure 8:
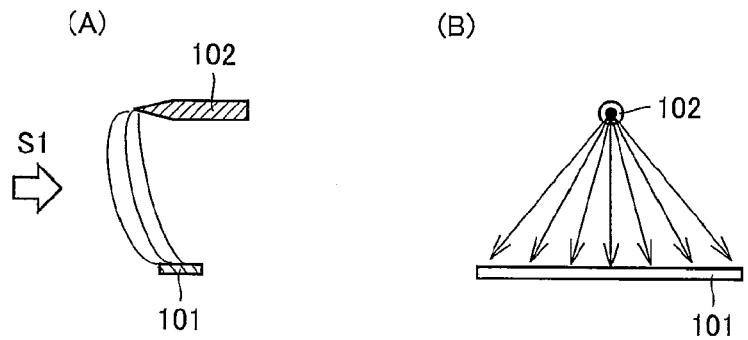
FIG. 8 (A) is a cross-sectional view for describing an electric field generated between a discharge electrode and an induction electrode in a corona discharge mechanism shown in Patent Document 2 (Japanese Patent Laying-Open No. 2003-308947), and FIG. 8 (B) is a drawing seen from a direction of an arrow S1 in FIG. 8 (A).

FIGS. 8 (A) and 8 (B) are diagrammatic illustrations for describing an electric field generated between a discharge electrode and an induction electrode in a corona discharge mechanism shown in Patent Document 2 (Japanese Patent Laying-Open No. 2003-308947). It is noted that FIG. 8 (A) is a cross-sectional view, and FIG. 8 (B) is a drawing seen from a direction of an arrow S1 in FIG. 8 (A).

With reference to FIGS. 8 (A) and 8 (B), in the corona discharge mechanism, an induction electrode 101 is disposed at a rearward lateral surface with respect to a needle-like tip of a discharge electrode 102, so that there is generated an electric field directed from the needle-like tip of discharge electrode 102 to induction electrode 101 located at the rearward lateral surface. Thereby directivity of an electric field distribution becomes nonuniform with respect to discharge electrode 102, and this nonuniform electric field causes nonuniform ion moving directions, so that ion emission efficiency is decreased and discharge at the tip of discharge electrode 102 becomes unstable, causing decrease in ion generation efficiency.

Figure 9:
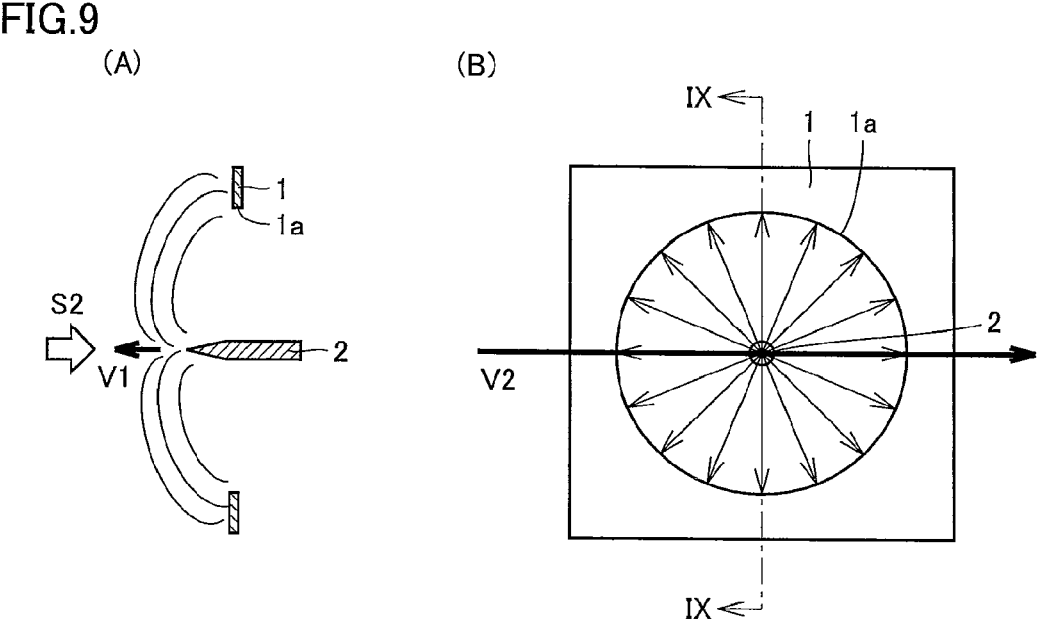
FIG. 9 (A) is a cross-sectional view for describing an electric field generated between the discharge electrode and the induction electrode in the ion-generating element in the embodiment of the present invention, and FIG. 9 (B) is a drawing seen from a direction of an arrow S2 in FIG. 9 (A).

FIGS. 9 (A) and 9 (B) are diagrammatic illustrations for describing an electric field generated between the discharge electrode and the induction electrode in the ion-generating element in the embodiment of the present invention. It is noted that FIG. 9 (A) is a cross-sectional view, and FIG. 9 (B) is a drawing seen from a direction of an arrow S2 in FIG. 9 (A). FIG. 9 (A) is a schematic cross-sectional view taken along a line IX-IX in FIG. 9 (B).

With reference to FIGS. 9 (A) and 9 (B), according to the present embodiment, the tip of discharge electrode 2 penetrates circular through hole 1a of induction electrode 1, and an outer portion (the entire outer peripheral surface) of discharge electrode 2 is surrounded by induction electrode 1. Therefore, an electric field is generated from the needle-like tip of discharge electrode 2, which serves as the center, toward induction electrode 1 along the entire circumference, namely, over 360° in plan view. It is thereby possible to suppress nonuniformity of directivity of an electric field distribution. Therefore, it is possible to suppress nonuniform ion moving directions caused by the nonuniform electric field distribution, so that it is possible to improve ion emission efficiency and cause stable discharge at the tip of discharge electrode 2, resulting in improvement in ion generation efficiency.

Further, in plan view, by disposing the needle-like tip of discharge electrode 2 at the center of through hole 1a having a shape of approximately a perfect circle, the distance between the needle-like tip of discharge electrode 2 and the outer peripheral portion of circular through hole 1a is kept constant along the entire circumference of through hole 1a. It is thereby possible to uniformize the electric field, which is generated between the needle-like tip of discharge electrode 2 and induction electrode 1, over 360°, and further suppress nonuniformity of an electric field distribution.

Further in the present embodiment, by allowing the needle-like tip of discharge electrode 2 to protrude upward with respect to the upper surface of induction electrode 1, ion emission efficiency can be improved. This feature will hereinafter be described.

Figure 10:
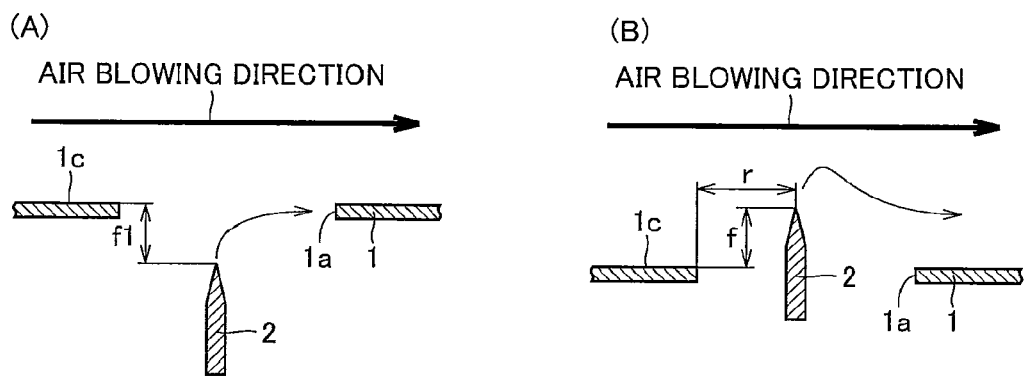
FIG. 10 (A) is a diagrammatic illustration for describing a behavior of ions in the case where a needle-like tip of the discharge electrode is retracted with respect to the induction electrode, and FIG. 10 (B) is a diagrammatic illustration for describing a behavior of ions in the case where the needle-like tip of the discharge electrode protrudes with respect to the induction electrode.

FIG. 10 includes a diagrammatic illustration (A) for describing a behavior of ions in the case where the needle-like tip of the discharge electrode is retracted with respect to the induction electrode, and a diagrammatic illustration (B) for describing a behavior of ions in the case where the needle-like tip of the discharge electrode protrudes with respect to the induction electrode.

With reference to FIG. 10 (A), in the case where the needle-like tip of discharge electrode 2 is retracted with respect to upper surface 1c of induction electrode 1 by a distance f1, the ions generated by discharge cannot ride the blown air stream flowing in a direction of an arrow in the drawing, unless it passes through through hole 1a of induction electrode 1. However, when the ions are to pass through through hole 1a of induction electrode 1, they are attracted toward induction electrode 1 side by the force of an electric field, and trapped by induction electrode 1. Ion emission efficiency is thereby decreased.

With reference to FIG. 10 (B), in the present embodiment, the needle-like tip of discharge electrode 2 protrudes upward with respect to the upper surface of induction electrode 1 by distance f. Therefore, the ions generated by discharge can ride the blown air stream flowing in a direction of an arrow in the drawing, even if they do not pass through through hole 1a of induction electrode 1. Therefore, although positive ions or negative ions generated in the vicinity of the needle-like tip of discharge electrode 2 are attracted to induction electrode 1 side by the force of an electric field, they ride a wind by means of the blown air, so that they are emitted to a space without being trapped by induction electrode 1. It is thereby possible to emit positive or negative ions on the blown air to a space before they are attracted by induction electrode 1 and neutralized. Accordingly, an amount of ions emitted to a space is increased, and efficiency for emitting ions to a space can be improved.

Further, the present inventor studied a length by which the needle-like tip of discharge electrode 2 protrudes from upper surface 1c of induction electrode 1 (hereinafter referred to as a "protruding length"). The details and the results thereof will hereinafter be described.

Initially, as shown in FIG. 10 (B), in the configuration in which the needle-like tip of discharge electrode 2 is positioned to protrude with respect to the upper surface 1c of induction electrode 1, measurement was conducted on changes in ion concentration obtained when radius r of through hole 1a of induction electrode 1 and protruding length f of discharge electrode 2 were changed. The results are shown in FIG. 11.

Figure 11:
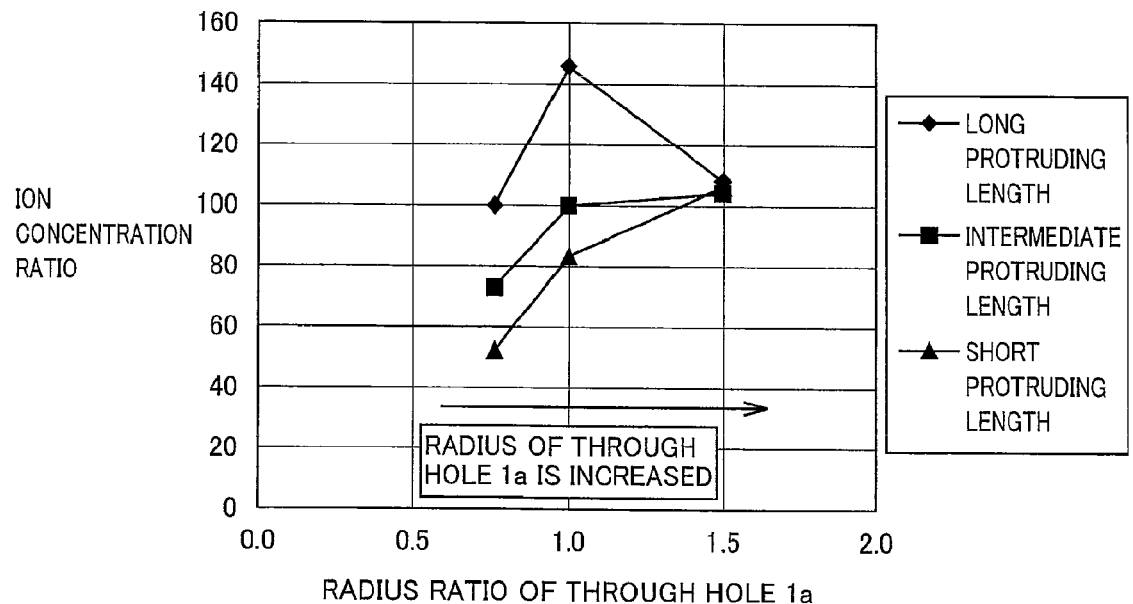
FIG. 11 is a diagram that shows the results of measurement of changes in ion concentration obtained when a radius r of the through hole of the induction electrode and a protruding length f of the discharge electrode are changed in the configuration in which the needle-like tip of the discharge electrode is positioned to protrude with respect to the upper surface of the induction electrode.

The results in FIG. 11 show an ion concentration ratio at a certain point in the space when the protruding length was changed in three steps including "long", "intermediate", and "short", and radius r of through hole 1a is also changed in three steps including "large", "intermediate", and "small".

The results in FIG. 11 show that when radius r of through hole 1a was "small" and "intermediate", longer protruding length f caused higher ion concentration. In contrast, when radius r of through hole 1a was "large", the ion concentration hardly changed even if protruding length f was increased. In other words, it was found that, when through hole 1a had small radius r, an ion-increasing effect became significant by increasing protruding length f, whereas when through hole 1a had large radius r, an ion-increasing effect was small even by increasing protruding length f.

Figure 12:
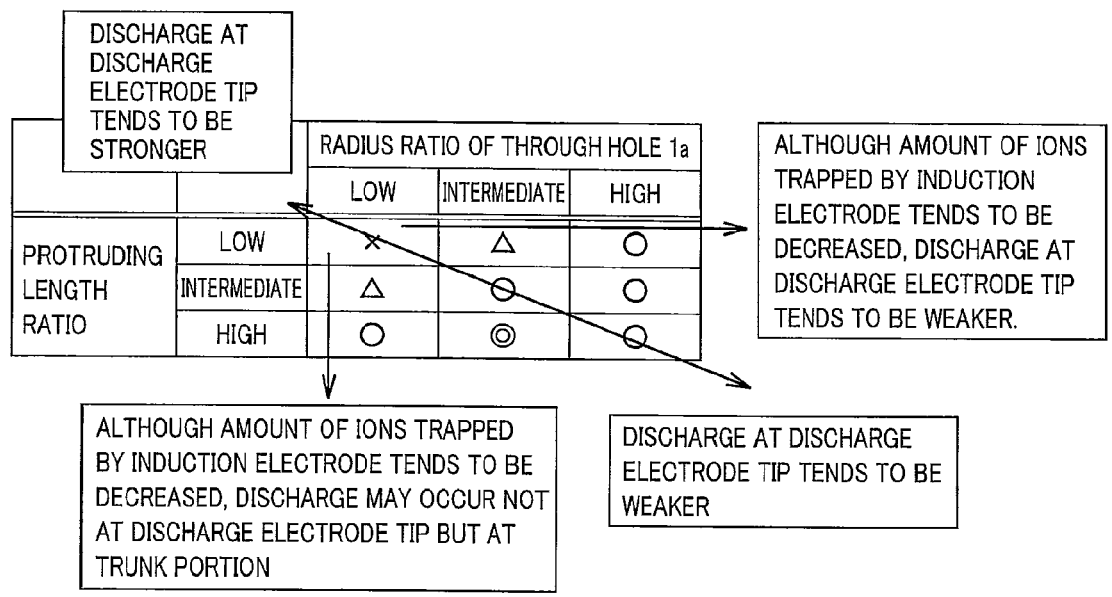
FIG. 12 is a diagram that comprehensively represents in table form the relation between protruding length f and radius r of through hole 1a, which is obtained from the results in FIG. 11.

Based on the results in FIG. 11, the relation between protruding length f and radius r of through hole 1a is comprehensively represented in table form as shown in FIG. 12. With reference to FIG. 12, the combination of small radius r of through hole 1a and short protruding length f (the upper left direction in the table) causes the strongest discharge at the tip of the discharge electrode. If both of radius r of through hole 1a and protruding length f are excessively decreased, excessively strong discharge occurs, resulting in that spark discharge may occur. In contrast, the combination of large radius r of through hole 1a and long protruding length f (the lower right direction in the table) causes the weakest discharge at the tip of the discharge electrode. If both of radius r of through hole 1a and protruding length f are excessively increased, discharge may not occur.

Large radius r of through hole 1a (the right direction in the table) means that the distance between discharge electrode 2 and induction electrode 1 is increased, so that large radius r has an influence on intensity of discharge at the tip of discharge electrode 2 as described above, and also causes decrease in amount of ions trapped by induction electrode 1, which ions have been generated at the tip of discharge electrode 2.

Large protruding length f (the lower direction in the table) means that the distance between the tip of discharge electrode 2 and induction electrode 1 is increased, so that large protruding length f has an influence on intensity of discharge at the tip of discharge electrode 2 as described above, and also causes decrease in amount of ions trapped by induction electrode 1, which ions have been generated at the tip of discharge electrode 2.

In the combination of small radius r of through hole 1a and long protruding length f (the lower left direction in the table), if protruding length f is excessively long with respect to radius r of through hole 1a, discharge occurs not at the tip of discharge electrode 2, but at a trunk portion of discharge electrode 2, at which the distance from induction electrode 1 is the shortest, resulting in a non-preferable state.

Both of two parameters, namely, protruding length f and radius r of through hole 1a, are effective for increasing an ion concentration. However, larger radius r of through hole 1a causes decrease in amount of ions trapped by induction electrode 1, and thus when radius r is large, the effect of increasing protruding length f becomes small.

Based on the results in FIGS. 11 and 12, making an appropriate combination of radius r of through hole 1a and protruding length f in association with the size of the entire ion-generating device is effective for implementing increase in ion concentration and implementing a thin and compact ion-generating device.

Figure 13:
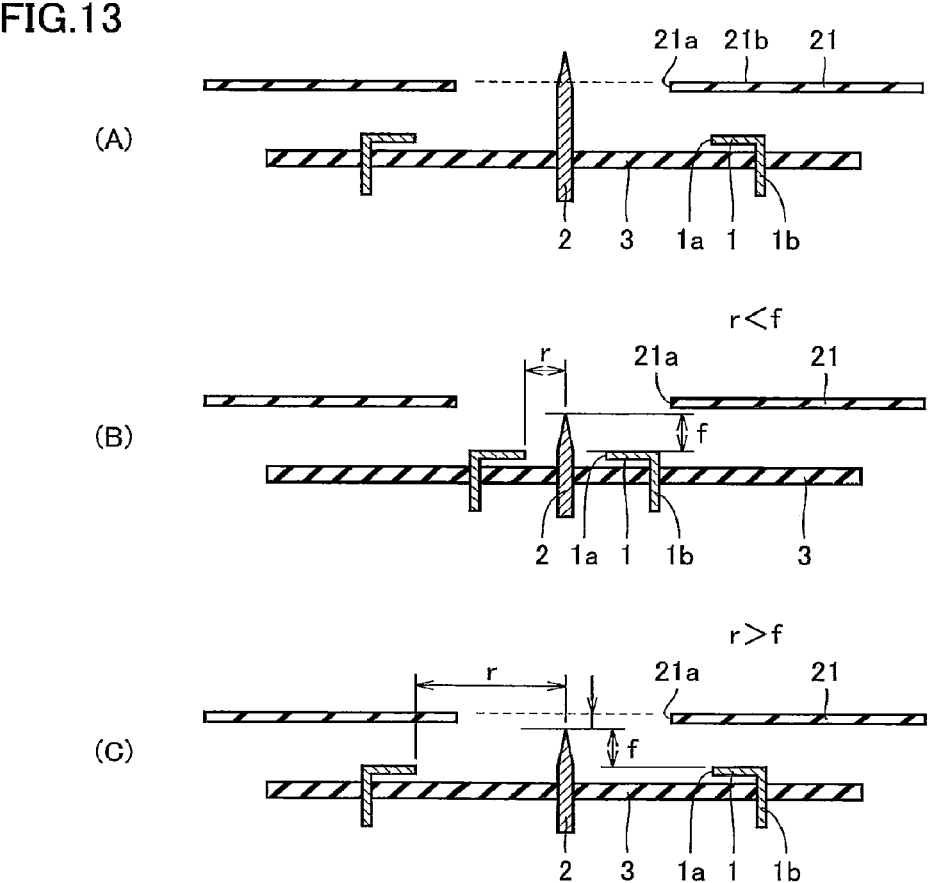
FIG. 13 (A) is a schematic cross-sectional view that shows a configuration of an ion-generating element having a different protruding length of the discharge electrode, showing the state where the tip of the discharge electrode protrudes upward with respect to the top plate.

When ion-generating elements 10a, 10b are to be disposed and configured in thin and compact ion-generating device 30 in view of these characteristics, larger protruding length f tends to cause a higher ion concentration. However, as shown in FIG. 13 (A), excessively long protruding length f results in that the needle-like tip of discharge electrode 2 protrudes from outer casing 21 of ion-generating device 30. In this case, ion generation performance of discharge electrode 2 is lowered by a mechanical impact. Therefore, the needle-like tip of discharge electrode 2 is preferably disposed such that it protrudes with respect to a surface of induction electrode 1, and that it does not protrude from the upper surface of top plate 21b of outer casing 21 of ion-generating device 30.

Further, as shown in FIG. 13 (B), even in the case where the needle-like tip of discharge electrode 2 does not protrude from the upper surface of top plate 21b of outer casing 21 of ion-generating device 30, if protruding length f becomes longer than radius r of through hole 1a, discharge occurs not at the needle-like tip of discharge electrode 2, but at the trunk portion of discharge electrode 2, at which the distance from induction electrode 1 is the shortest, resulting in a non-preferable state. Therefore, as shown in FIG. 13 (C), protruding length f is more preferably shorter than radius r of through hole 1a.

The discharge phenomenon is simply determined by an applied voltage and a distance between electrodes. Therefore, if the tip of discharge electrode 2 has no acute-angled portion, discharge occurs at a portion where the distance between induction electrode 1 and discharge electrode 2 is minimized.

However, if the tip of discharge electrode 2 has a needle-like shape and is pointed at an acute angle, an electric field concentrates on the tip of discharge electrode 2, and corona discharge occurs between the tip and induction electrode 1. In other words, by allowing the tip of discharge electrode 2 to have an acute angle, a potential gradient (electric field intensity) at the tip becomes strong, so that it becomes possible to cause corona discharge between the tip of discharge electrode 2 and induction electrode 1 even if the distance between the tip and induction electrode 1 is not minimized.

Here, the present inventor has found that, if the tip of discharge electrode 2 is allowed to have a needle-like shape to have an acute-angled portion, and if protruding length f is shorter than radius r of through hole 1a, corona discharge occurs between the needle-like tip of discharge electrode 2 and induction electrode 1. Therefore, by setting protruding length f to be shorter than radius r of through hole 1a, it is possible to occur corona discharge between the needle-like tip of discharge electrode 2 and induction electrode 1, and prevent discharge between the trunk portion of discharge electrode 2 and induction electrode 1.

It is noted that the protruding length is, for example, 0.5 mm-4.0 mm, and preferably 1 mm-2 mm. The diameter of through hole 1a of induction electrode 1 is, for example, $\phi$112 mm-$\phi$13 mm (a radius of through hole 1a is 6 mm-6.5 mm).

Furthermore, the present inventor studied distance e (see FIG. 2) between the flat plate portion of induction electrode 1 and supporting substrate 3. The details and the results thereof will hereinafter be described.

Figure 14:
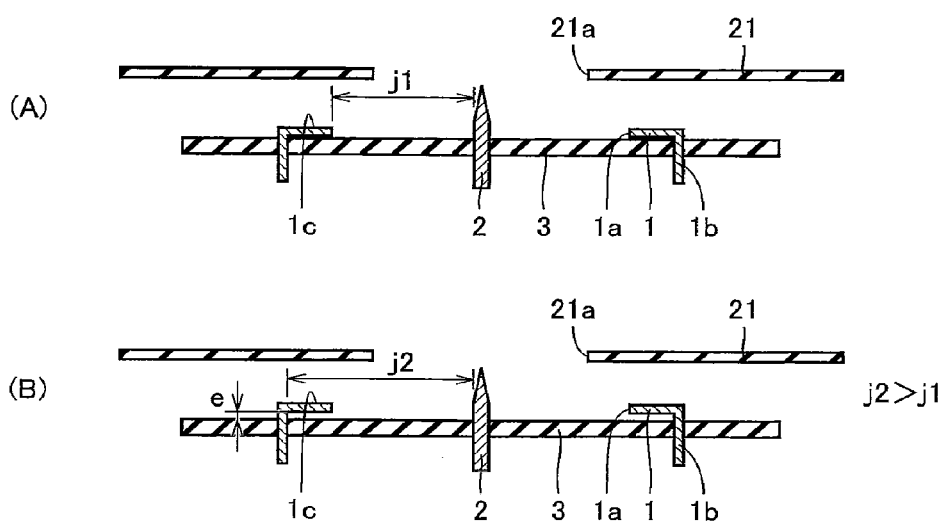
FIG. 14 (A) is a schematic cross-sectional view of the ion-generating element, showing the state where a distance e between a flat plate portion of the induction electrode and a supporting substrate is 0, and FIG. 14 (B) is a schematic cross-sectional view of the ion-generating element, showing the state distance e is ensured.

FIG. 14 includes schematic cross-sectional views of the ion-generating element in the case (A) where distance e between the flat plate portion of the induction electrode and the supporting substrate is 0, and in the case (B) where distance e is ensured.

The most efficient way to dispose induction electrode 1 and discharge electrode 2 on the same supporting substrate 3, allow the tip of discharge electrode 2 to protrude upward with respect to upper surface 1c of the flat plate portion of induction electrode 1, and make ion-generating device 30 thin is to closely attach induction electrode 1 to the surface of supporting substrate 3 as shown in FIG. 14 (A).

In this case, however, a creeping distance j1 along the surface of supporting substrate 3 between discharge electrode 2 and induction electrode 1 is approximately equal to radius r of through hole 1a. A high voltage is applied between discharge electrode 2 and induction electrode 1, and hence if creeping distance j1 is short, there may be a risk of creeping discharge. Therefore, there should be ensured a margin for the distance between discharge electrode 2 and induction electrode 1, which are disposed on the same supporting substrate 3.

Therefore, as shown in FIG. 14 (B), by providing bent portion 1b at each of the opposite end portions of induction electrode 1, and allowing supporting substrate 3 to support induction electrode 1 at bent portion 1b, a gap having dimension e is ensured between the flat plate portion of induction electrode 1 and supporting substrate 3. Thereby a creeping distance j2 along the surface of supporting substrate 3 between discharge electrode 2 and induction electrode 1 becomes longer than distance j1 shown in FIG. 14 (A). By always ensuring a distance equal to or longer than a certain distance between the flat plate portion of induction electrode 1 and supporting substrate 3 as such, it is possible to suppress unnecessary creeping discharge. Dimension e of the gap is, for example, 0.5 mm-2.0 mm.

It is noted that, by disposing induction electrode 1 and discharge electrode 2 on the same supporting substrate 3, it is possible to control a planar displacement of, and also minimize a displacement in a height direction of induction electrode 1 and discharge electrode 2. It is thereby possible to reduce the causes of an error of the positional relation between induction electrode 1 and discharge electrode 2.

As described above, according to the present embodiment, it is possible to achieve stable ion generation, decrease the rate at which generated ions are neutralized by induction electrode 1, and efficiently emit ions from the apparatus to a space in a significantly larger amount than conventional.

Furthermore, it is possible to implement a thin and compact ion-generating device in which a high voltage drive circuit and the ion-generating element are integrated, so that it is possible to increase the range of uses of an electrical apparatus mounted with the ion-generating device, and increase the degree of freedom of the sites where the ion-generating device is to be mounted.

It should be understood that the embodiment disclosed herein is illustrative and not limitative in all aspects. The scope of the present invention is shown not by the description above but by the scope of the claims, and is intended to include all modifications within the equivalent meaning and scope of the claims.

INDUSTRIAL APPLICABILITY

The present invention can particularly advantageously be applied to an ion-generating device including an induction electrode and a discharge electrode having a needle-like tip, for generating ions by discharge, and an electrical apparatus provided with the ion-generating device.

Description of the Reference Signs

1: induction electrode, 1a: through hole, 1b: bent portion, 1c: upper surface, 2: discharge electrode, 3: supporting substrate, 3a, 3b: through hole, 10a, 10b: ion-generating element, 11: high-voltage transformer, 12a, 12b: high-voltage circuit, 21: outer casing, 21a: ion-emitting hole, 21b: top plate, 22: power supply input connector, 23: power supply circuit, 30: ion-generating device, 31: molding resin, 60: air-cleaning unit, 61: front panel, 62: body, 63: outlet port, 64: air intake port, 65: fan casing.

The invention claimed is:

1. An ion-generating device for generating ions by discharge, comprising:
   a discharge electrode having a needle-like tip;
   an induction electrode having a flat plate portion at which a circular through hole is made; and
   a casing in which said discharge electrode and said induction electrode are disposed,
   wherein
   said tip of said discharge electrode penetrating said through hole of said induction electrode, and protruding upward with respect to an upper surface of said flat plate portion of said induction electrode,
   said casing has a top plate at which an ion-emitting hole in communication with said through hole of said induction electrode is formed, and
   said tip of said discharge electrode is disposed such that said tip does not protrude upward with respect to a top surface of said top plate.

2. The ion-generating device according to claim 1, wherein a length by which said tip of said discharge electrode protrudes upward with respect to said upper surface of said flat plate portion of said induction electrode is shorter than a radius of said through hole.

3. The ion-generating device according to claim 1, further comprising a supporting substrate supporting said induction electrode, wherein
   said induction electrode has a bent portion made by bending said flat plate portion and supported by said supporting substrate, and
   said induction electrode is supported by said supporting substrate such that a gap is made between said flat plate portion of said induction electrode and said supporting substrate.

4. An electrical apparatus, comprising:
   the ion-generating device recited in claim 1; and
   an air blow unit for delivering at least any of positive ions and negative ions generated at said ion-generating device on a blown air stream to an outside of the electrical apparatus.

5. An ion-generating device for generating ions by discharge, comprising:
   an ion-generating element including a discharge electrode having a needle-like tip, and an induction electrode having a flat plate portion at which a circular through hole is made;
   a high-voltage transformer for supplying a high voltage to said ion-generating element;
   a high voltage-generating circuit for driving said high-voltage transformer;
   a power supply input connector electrically connected to said high voltage-generating circuit; and
   a casing in which said ion-generating element, said high-voltage transformer, said high voltage-generating circuit, and said power supply input connector are disposed,
   said tip of said discharge electrode penetrating said through hole of said induction electrode, and protruding upward with respect to an upper surface of said flat plate portion of said induction electrode, and
   said ion-generating element, said high-voltage transformer, said high voltage-generating circuit, and said power supply input connector being disposed in a planar manner with respect to one another, and disposed in said casing in an integrated manner.

6. The ion-generating device according to claim 5, wherein
   said discharge electrode and said induction electrode are disposed in said casing,
   said casing has a top plate at which an ion-emitting hole in communication with said through hole of said induction electrode is formed, and
   said tip of said discharge electrode is disposed such that said tip does not protrude upward with respect to a top surface of said top plate.

7. The ion-generating device according to claim 5, wherein a length by which said tip of said discharge electrode protrudes upward with respect to said upper surface of said flat plate portion of said induction electrode is shorter than a radius of said through hole.

8. The ion-generating device according to claim 5, further comprising a supporting substrate supporting said induction electrode, wherein
   said induction electrode has a bent portion made by bending said flat plate portion and supported by said supporting substrate, and
   said induction electrode is supported by said supporting substrate such that a gap is made between said flat plate portion of said induction electrode and said supporting substrate.

9. An electrical apparatus, comprising:
   the ion-generating device recited in claim 5; and an air blow unit for delivering at least any of positive ions and negative ions generated at said ion-generating device on a blown air stream to an outside of the electrical apparatus.

* * * * *